US00PP31296P3

(12) United States Plant Patent
Larse

(10) Patent No.: US PP31,296 P3
(45) Date of Patent: Dec. 31, 2019

(54) STRAWBERRY PLANT NAMED 'DR. DUNCAN'

(50) Latin Name: ***Fragaria* x *ananassa***
Varietal Denomination: Dr. Duncan

(71) Applicant: Sweet Darlings Sales, Inc., Aptos, CA (US)

(72) Inventor: John Larse, Watsonville, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 0 days.

(21) Appl. No.: 15/932,840

(22) Filed: May 4, 2018

(65) Prior Publication Data

US 2019/0343029 P1 Nov. 7, 2019

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

*Primary Examiner* — Kent L Bell
(74) *Attorney, Agent, or Firm* — Cooley LLP

(57) ABSTRACT

The present invention provides new and distinct strawberry plant designated as 'Dr. Duncan' (a.k.a. '108637').

8 Drawing Sheets

Latin name of the genus and species: *Fragaria* x *ananassa.*

Varietal denomination: 'Dr. Duncan' (a.k.a. '108637').

BACKGROUND OF THE INVENTION

The present invention relates to new and distinct strawberry plant designated as 'Dr. Duncan' (a.k.a. '108637').

'Dr. Duncan' (a.k.a. '108637') is the result of a controlled-cross made in Nov. 18, 2010 between a female parent cultivar designated '107801' (a.k.a. 'Akira') and a male parent cultivar designated '1038578' made by the Inventor and was first fruited in Watsonville, Calif. growing fields. Following selection and during testing, the plant was originally designated '108637' and subsequently named 'Dr. Duncan'. 'Dr. Duncan' is a day-neutral plant.

This new strawberry plant was asexually reproduced via runners (stolons) by the inventor at Watsonville, Calif. Asexual propagules from the original source have been tested in Watsonville growing fields and to a limited extent, grower fields in high elevation. The properties of this plant were found to be transmissible by such asexual reproduction. The plant is stable and reproduces true to type in successive generations of asexual reproduction.

BRIEF SUMMARY OF THE INVENTION

This invention relates to new and distinctive strawberry plant designated as 'Dr. Duncan' (a.k.a. '108637'). The plant is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

'Dr. Duncan' has not been observed under all possible environmental conditions, and the phenotype may vary significantly with variations in environment, however with no variance in genotype. The following observations, measurements, and comparisons describe this plant as grown under normal conditions in Watsonville, Calif. unless otherwise noted.

The following traits and photographs in combination distinguish strawberry plant 'Dr. Duncan' from known strawberry plants. Plants for the botanical measurements in the present application were grown as annuals. Any color references are made to The Royal Horticultural Society Colour Chart, 1995 Edition, except where general terms of ordinary dictionary significance are used. The plants were 8-month old when the observation was made.

TABLE 1

'Dr. Duncan' Characteristics

| | Characteristic | Description |
|---|---|---|
| General | Plant Habit | Perennial |
| | Plant Growth Habit | Semi-upright |
| | Day length | Day Neutral |
| | Planting season | Fall |
| | Height | 29 cm |
| | Width | 44 cm |
| | Density of foliage | Medium |
| | Plant vigor | Moderate |
| | Rain/weather tolerance | Low to Moderate |
| | Harvest Ease | Easy |
| | Crown diameter | 4 cm |
| | Fertility | Self-fertile |
| | Freezing quality | moderate |
| Leaf | Leaf Shape | Concave |
| | Leaf blistering | weak |
| | Leaf glossiness | medium |
| | Leaf variegation | absent |
| | Leaflets per leaf | 3 |
| | Number of leaflets | 113 |

TABLE 1-continued

'Dr. Duncan' Characteristics

| | Characteristic | Description |
|---|---|---|
| | Terminal leaflet width | 72 mm |
| | Terminal leaflet length | 84 mm |
| | Terminal leaflet length/width ratio | 1.17 |
| | Teeth per terminal leaflet | 18 to 23 |
| | Shape of terminal leaflet | Orbicular |
| | Shape of the terminal leaflet base | Acute |
| | Shape of terminal leaflet in cross-section | Concave |
| | Shape of the terminal leaflet margin | Serrate |
| | Color of upper side of leaflet | RHS 137A |
| | Color of lower side of leaflet | RHS 137C |
| | Terminal leaflet margin | flat |
| | Leaf blistering | Weak |
| | Leaf glossiness | Medium |
| | Leaf variegation | Absent |
| | Number of leaflets | 113 |
| | Terminal Leaflet margin | Flat |
| | Terminal Leaflet shape | Orbicular |
| | Terminal Leaflet shape of base | Acute |
| | Terminal Leaflet shape of apex | Rounded |
| | Leaflets per Leaf | 3 |
| | Shape of terminal leaflet | Orbicular |
| | Shape of the terminal leaflet apex | Rounded |
| Limbs | Petiole length | 21 cm |
| | Petiole diameter | 3.42 mm |
| | Petiole pubescence | Sparse |
| | Petiole pose of hairs | Horizontal |
| | Petiole color | RHS 144A |
| | Petiolule length | 1.3 cm |
| | Petiolule diameter | 2.56 mm |
| | Petiolule color (color code) | RHS 145B |
| | Stipule length | 3.7 cm |
| | Stipule width | 1.7 cm |
| | Stipule pubescence | Medium to Dense |
| | Stipule anthocyanin | Present |
| | Stipule color (color code) | RHS 145A |
| | Stipule anthocyanin color (color code) | RHS 184D |
| | Pedicel color (color code) | RHS 145A |
| | Pedicel length | 10.5 cm |
| | Pedicel diameter | 2.66 mm |
| | Attitude of hairs on petiole and pedicel | Slightly Outwards to Horizontal |
| | Peduncle size | Medium to Large |
| | Peduncle length | 25.5 cm |
| | Peduncle diameter | 3.71 mm |
| | Peduncle color (color code) | RHS 145B |
| | Peduncle pubescence | medium |
| | Attitude of hairs on peduncle and pedicel | Slightly outwards to horizontal |
| Inflorescence | Inflorescence position relative to foliage | Above |
| | Time of flowering (50% of plants in bloom) | April |
| | Flower arrangement of petals | Touching |
| | Flower size | Medium to Large |
| | Flower diameter | 2.5 cm |
| | Number of Flowers per Truss | 3 to 10 |
| | Petal shape | Orbicular |
| | Petal apex | Rounded |
| | Petal margin | Entire |
| | Petal base shape | Concave |
| | Petal spacing | Touching |
| | Petal length | 1.6 cm |
| | Petal width | 1.5 cm |
| | Petal length/width ratio | 1.07 |
| | Petal number per flower | 5 to 7 |
| | Number of flowers | 21 to 34 |
| | Upper Petal color | RHS 155C |
| | Lower Petal color | RHS 155D |

TABLE 1-continued

'Dr. Duncan' Characteristics

| | Characteristic | Description |
|---|---|---|
| | Calyx diameter | 3.1 to 4.2 cm |
| | Corolla diameter | 2.5 cm |
| | Calyx diameter relative to corolla | Larger |
| | Inner Calyx diameter relative to outer | Equal |
| | Sepal shape | Ellipitical |
| | Sepal apex | Convex |
| | Sepal margin | Entire |
| | Sepal number per flower | 9 to 15 |
| | Sepal length | 2 to 2.5 cm |
| | Sepal width | 1.0 to 1.1 cm |
| | Receptacle color | RHS 145B |
| | Self Fertility | Not Tested |
| | Time of flowering (50% of plants in bloom) | April |
| | Shape of stigma | Capitate |
| | Color of stigma | RHS 4A |
| | Length of style | 2 mm |
| | Color of style | RHS 12A |
| | Color of the ovary | RHS 145A |
| | Receptacle color | RHS 145B |
| | Number of stamen | 21 to 25 |
| | Length of the stamens | 2.0 to 3.5 mm |
| | Shape of anther | Dorsifixed |
| | Size of anther | 1.5 to 2.0 mm |
| | Color of anther | RHS 22A |
| | Anther diameter | 1.2 mm |
| | Anther length | 1.6 mm |
| | Amount of pollen | Moderate |
| | Color of pollen | RHS 13B |
| | Color of filament | RHS 145C |
| | Length of filament | 2.0 to 5.0 mm |
| Stolon | Stolon number | 2 to 3 |
| | Stolon anthocyanin | RHS 183A |
| | Stolon thickness | Thin to Moderate |
| | Stolon pubescence | Heavy |
| | Stolon Length | 72 cm |
| | Widest diameter of stolon at leaf attachment | 3.30 mm |
| | Stolon color | 145B |
| Fruit | Fruiting truss length | 7.0 to 13.0 cm |
| | Fruiting truss diameter | 3.76 mm |
| | Number of fruit per truss | 1 to 7 |
| | Shape difference between primary & secondary fruits | No difference |
| | Fruit calyx diameter | 5.9 cm |
| | Fruiting truss attitude | Horizontal to Slightly Outwards |
| | Truss color | RHS 145A |
| | Fruit length | 4.92 cm |
| | Fruit width | 4.22 cm |
| | Fruit skin color | RHS 145A |
| | Fruit flesh color excluding core | RHS 44A |
| | Fruit core color | RHS 41B |
| | Fruit length/width ratio | 1.17 |
| | Fruit weight | 23 g |
| | Relative fruit size | Medium |
| | Predominant fruit shape | Globose Conic |
| | Shape difference between primary & secondary fruits | No Shape Difference |
| | Width of band without of achenes | Medium |
| | Fruit glossiness | Medium to Strong |
| | Position of achenes | Even to Below Surface |
| | Achene color | RHS 145A |
| | Achenes per fruit | 325 |
| | Achene weight | 0.19 g |
| | Position of calyx | Even |
| | Level of adherence of calyx | Medium to Strong |
| | Color of calyx | RHS 136A |
| | Pose of calyx segments | Spreading to Reflexed |
| | Fruit calyx diameter | 5.9 cm |

TABLE 1-continued

'Dr. Duncan' Characteristics

| Characteristic | Description |
|---|---|
| Size of calyx in relation to fruit | Equal to Larger |
| Firmness of flesh | Medium |
| Color of the flesh | RHS 45A |
| Evenness of flesh color | Nearly Even |
| Fruit hollow core length | 2.4 cm |
| Fruit hollow core width | 0.8 cm |
| Fruit hollow length/width ratio | 3.00 |
| Hollow center | Medium |
| Sweetness (Brix) | 8 |
| Acidity (pH) | 3.78 |
| Texture when tasted | Fine |
| Time of flowering | April |
| Time of fruit ripening | May |
| Harvest maturity (50% of plants with ripe fruit) | May |
| Type of bearing | Day Neutral |
| Grams of fruit per plant (June) | 907 g |
| Firmness | Firm |
| Surface Texture | Smooth |
| Appearance Score (1 to 5 with 5 = best) | 4 |
| Storage longevity | 5 to 10 Days |
| Cull rate: 1- % Usable | 10% |
| Yield per plant per season | 2.6 kg |

'Albion' (U.S. Plant Pat. No. 16,228) is a commercial strawberry variety that is similar to, but distinguished from 'Dr. Duncan'. The fruit yield of 'Dr. Duncan' exceeds the yield of 'Albion' in multiple annual testing cycles performed at the breeders test location in Watsonville Calif. 'Dr. Duncan' does not produce large quantities of stolon (runners) during the fruiting period after propagation in California nurseries and Watsonville fruiting field, which saves labor of about $1,500 per acre because stolon must be removed in order to effect efficient harvest and continued flowering. 'Albion' produces abundant quantities of stolon that must be cut by hand labor in the fruiting field.

The fruit 'Dr. Duncan' is darker in redness coloration than its parent 'Akira'. The foliage of "Akira" is very dark green compared to the medium green coloration of the foliage of 'Dr. Duncan'. The foliage and plant structure of parent 'Akira' was observed to be more dense than the foliage of 'Dr. Duncan'.

The foliage and plant structure of the male parent of 'Dr. Duncan' was observed to be denser than the foliage of 'Dr. Duncan'. 'Dr. Duncan' has a significantly higher yield and a significantly higher percentage of marketable fruit compared to its male parent. The fruit of 'Dr. Duncan' is a much darker red and slightly smaller than the fruit of its female parent.

DESCRIPTION OF THE DRAWINGS

The accompanying color photographs depict various characteristics of the cultivars as nearly true as possible to make color reproductions.

Figure 1:
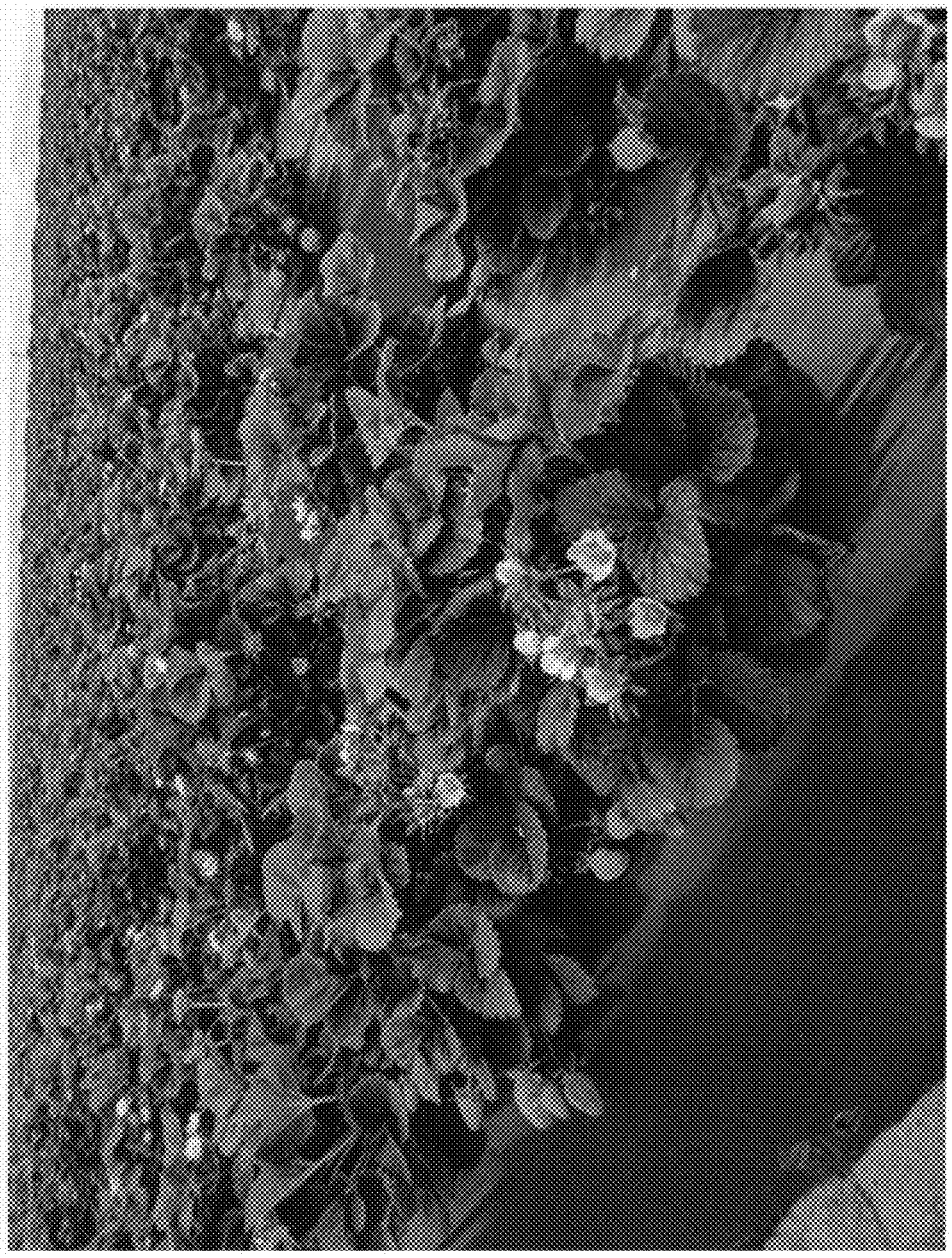
FIG. 1 shows 'Dr. Duncan' plants growing in the field with inflorescences in mid June about 8-month old.
Figure 2:
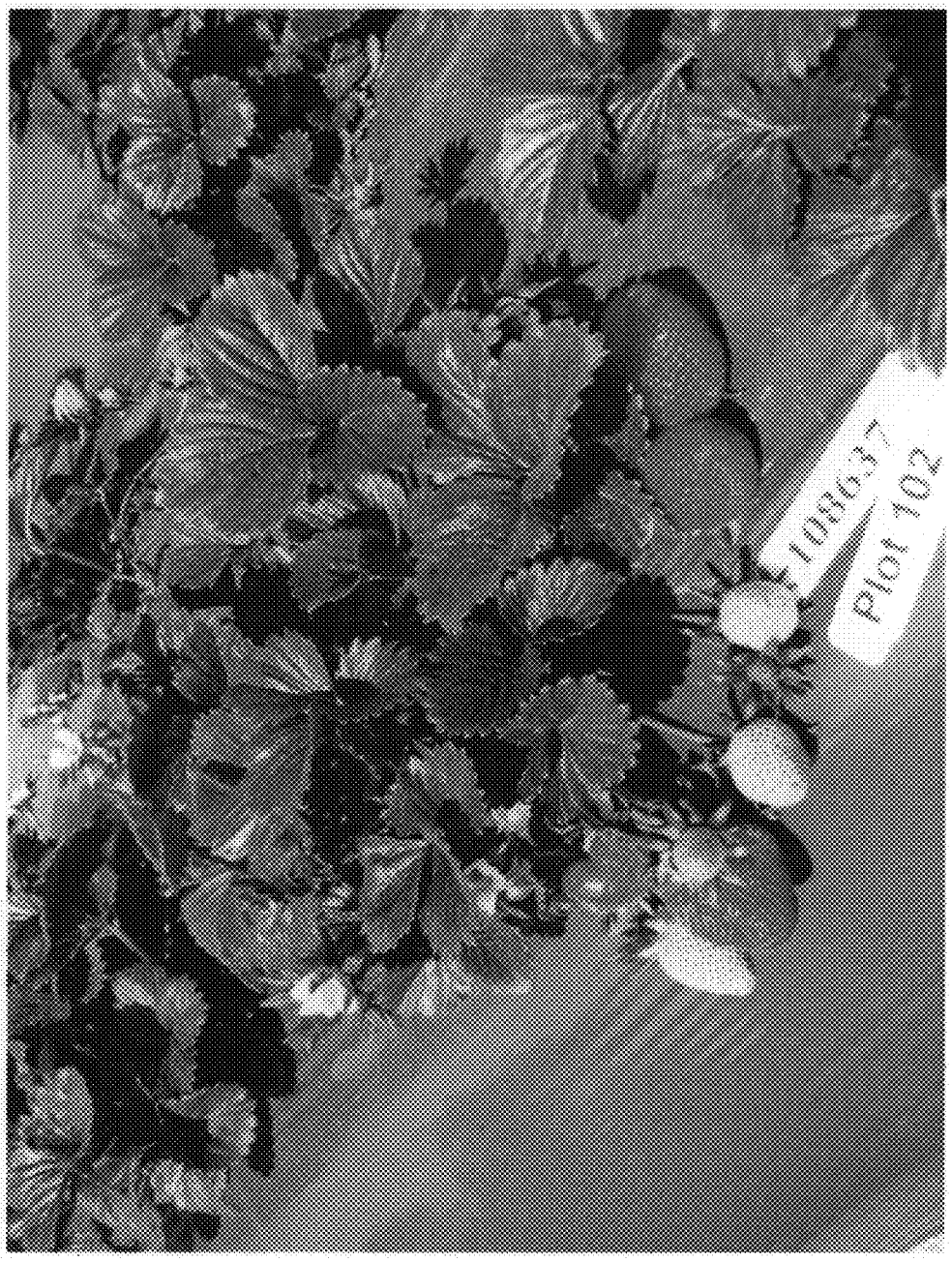
FIG. 2 shows 'Dr. Duncan' plants growing in the field with multiple fruits.
Figure 3:
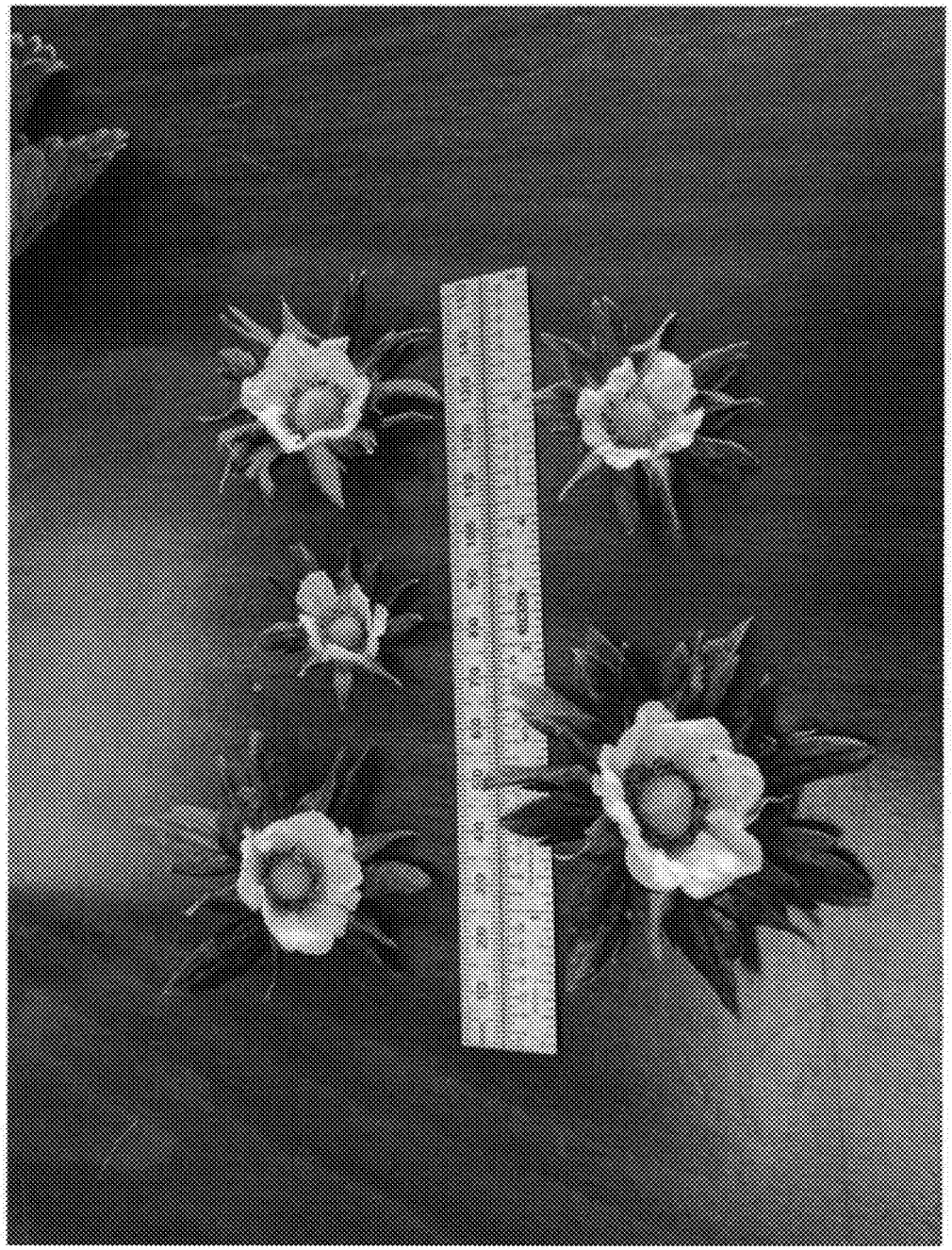
FIG. 3 shows the front side of inflorescences of 'Dr. Duncan' plants.
Figure 4:
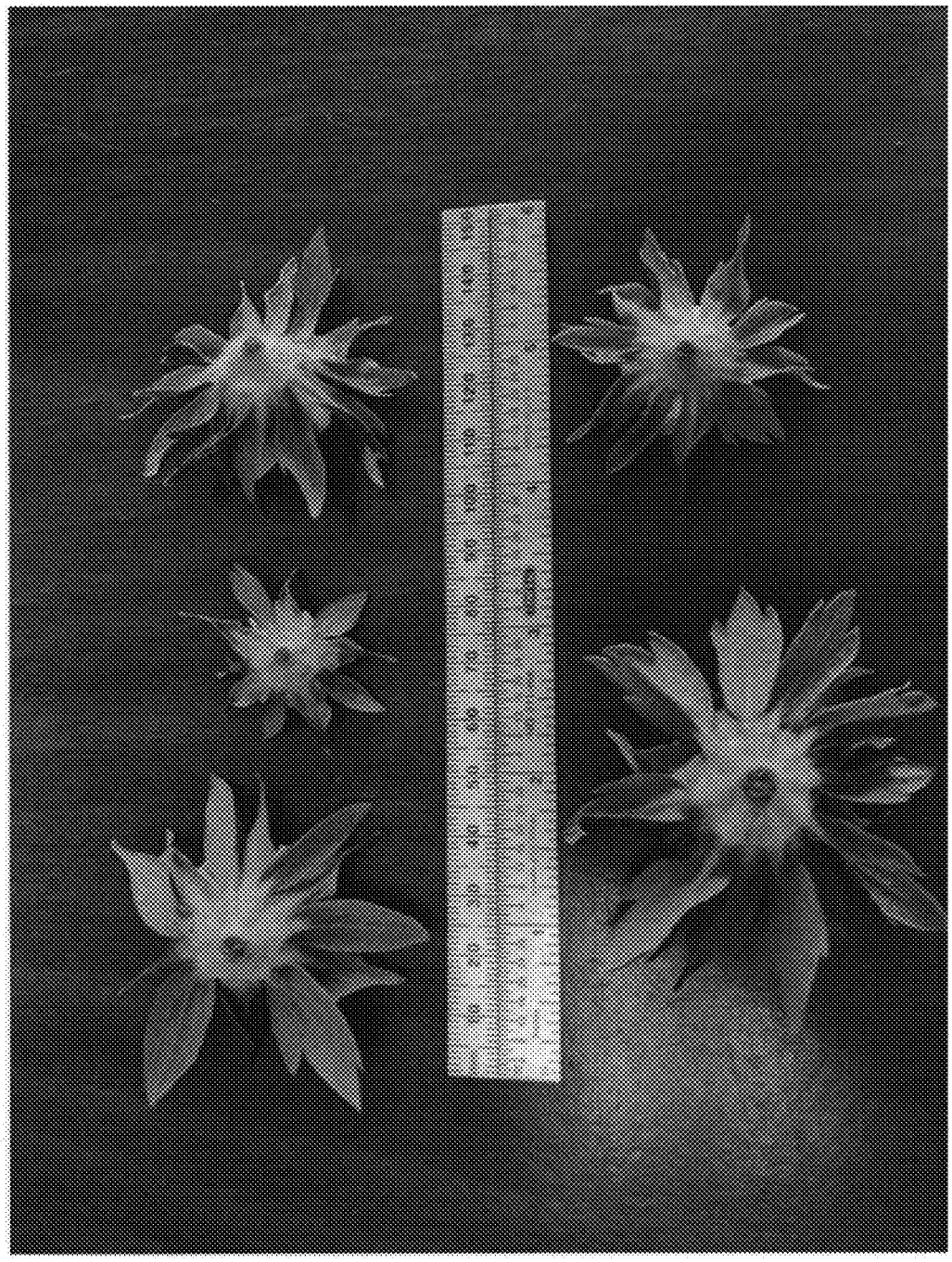
FIG. 4 shows the back side of inflorescences of 'Dr. Duncan' plants.
Figure 5:
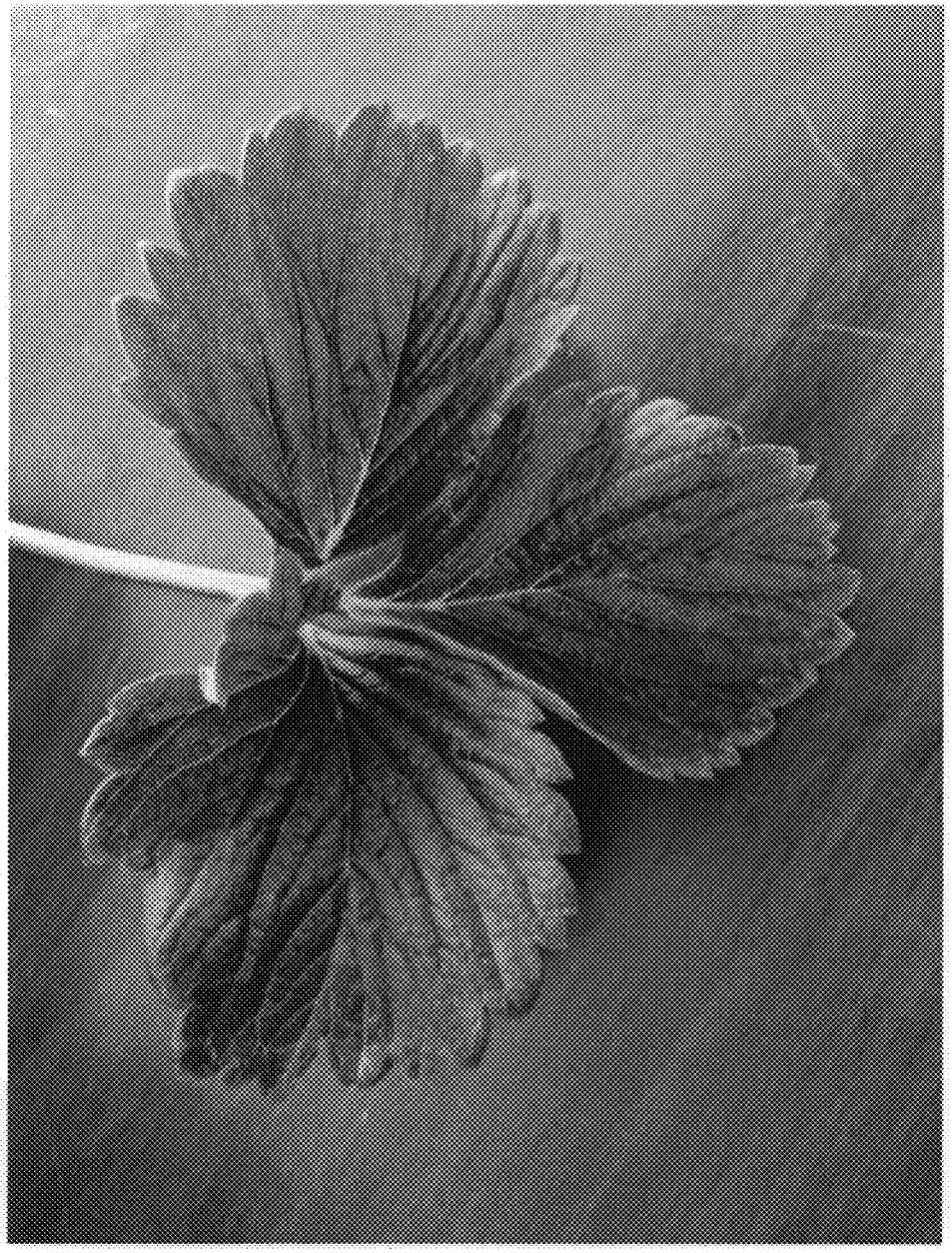
FIG. 5 shows the front side of a leaf of 'Dr. Duncan' plants.
Figure 6:
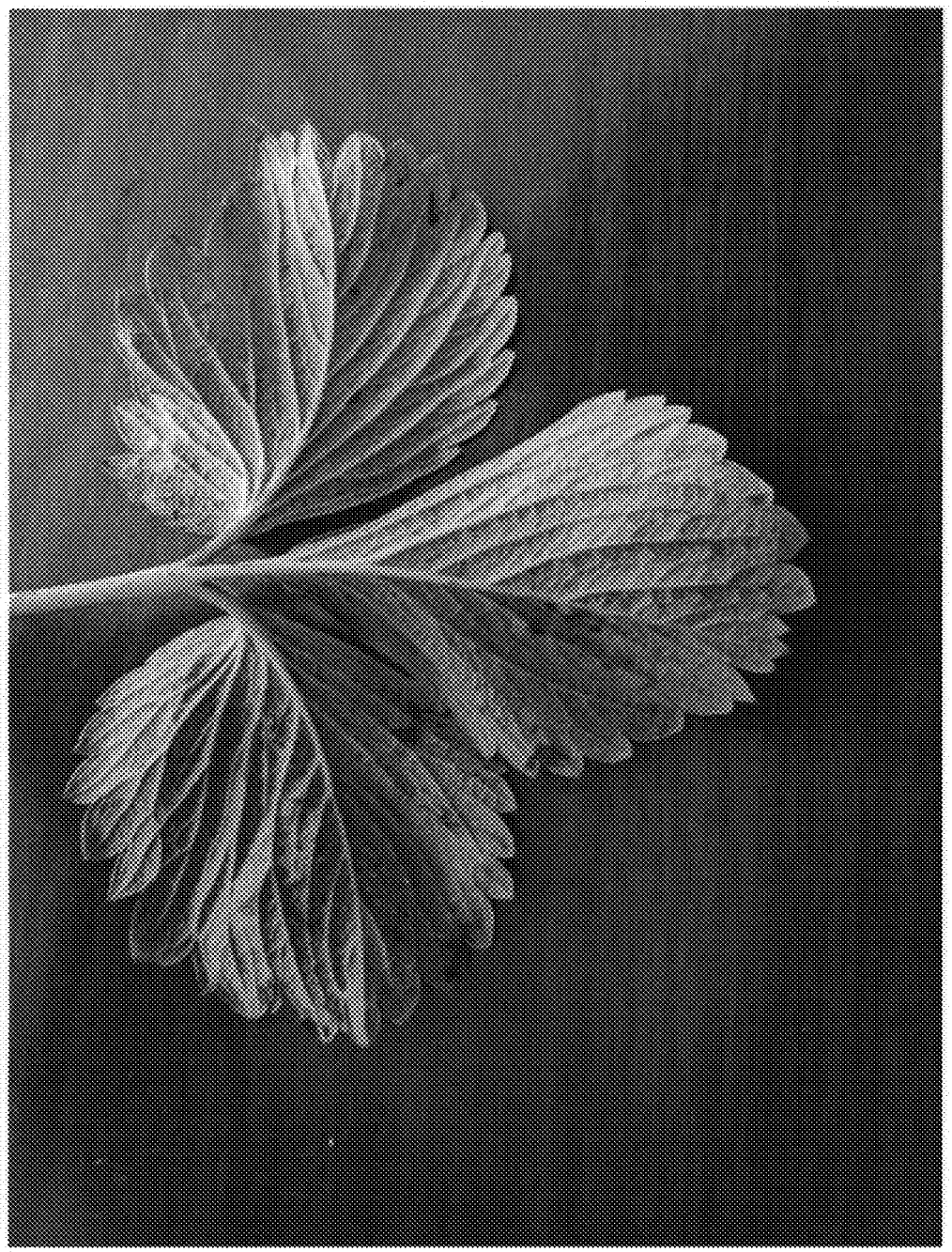
FIG. 6 shows the back side of a leaf of 'Dr. Duncan' plants.
Figure 7:
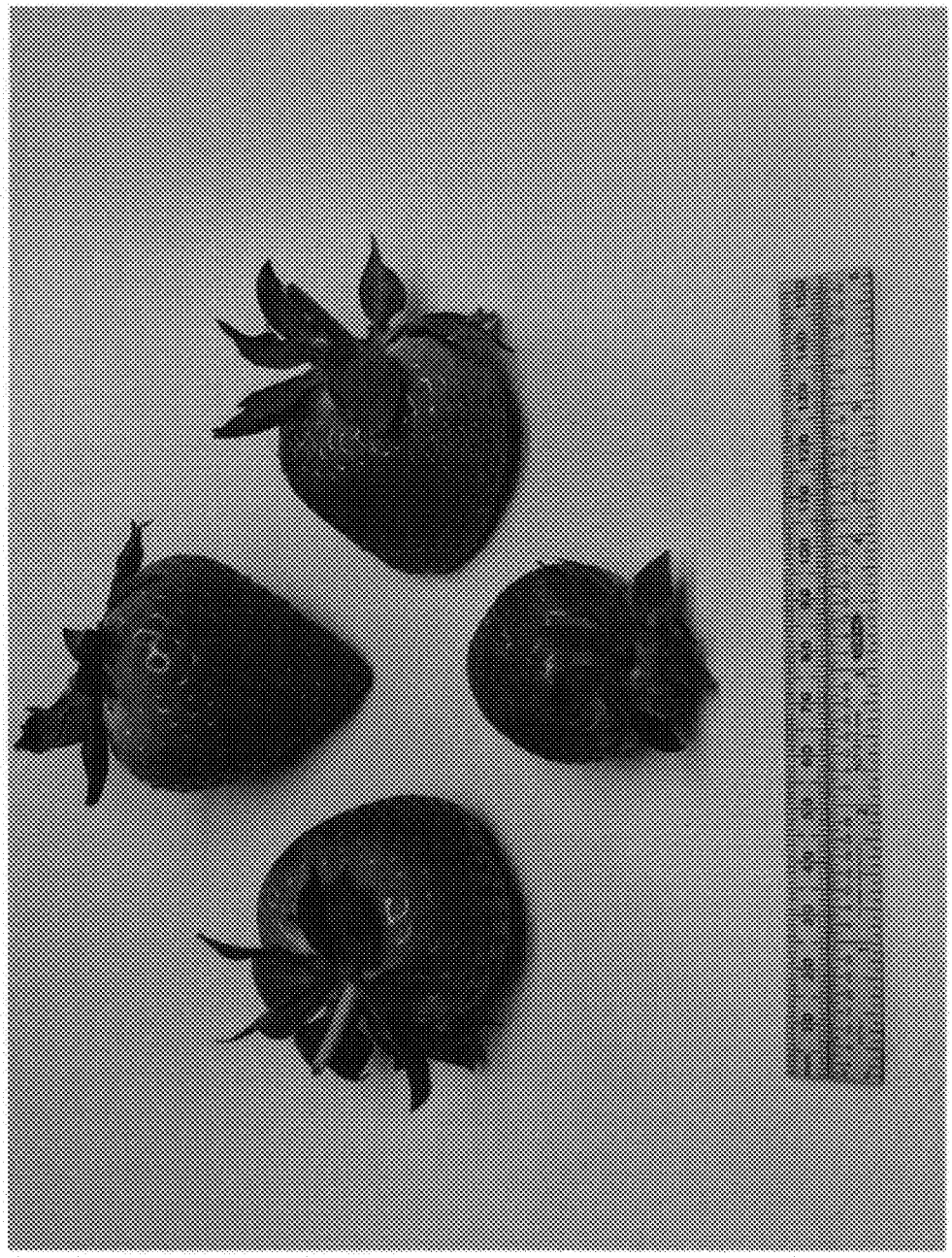
FIG. 7 shows fruits of 'Dr. Duncan' plants.
Figure 8:
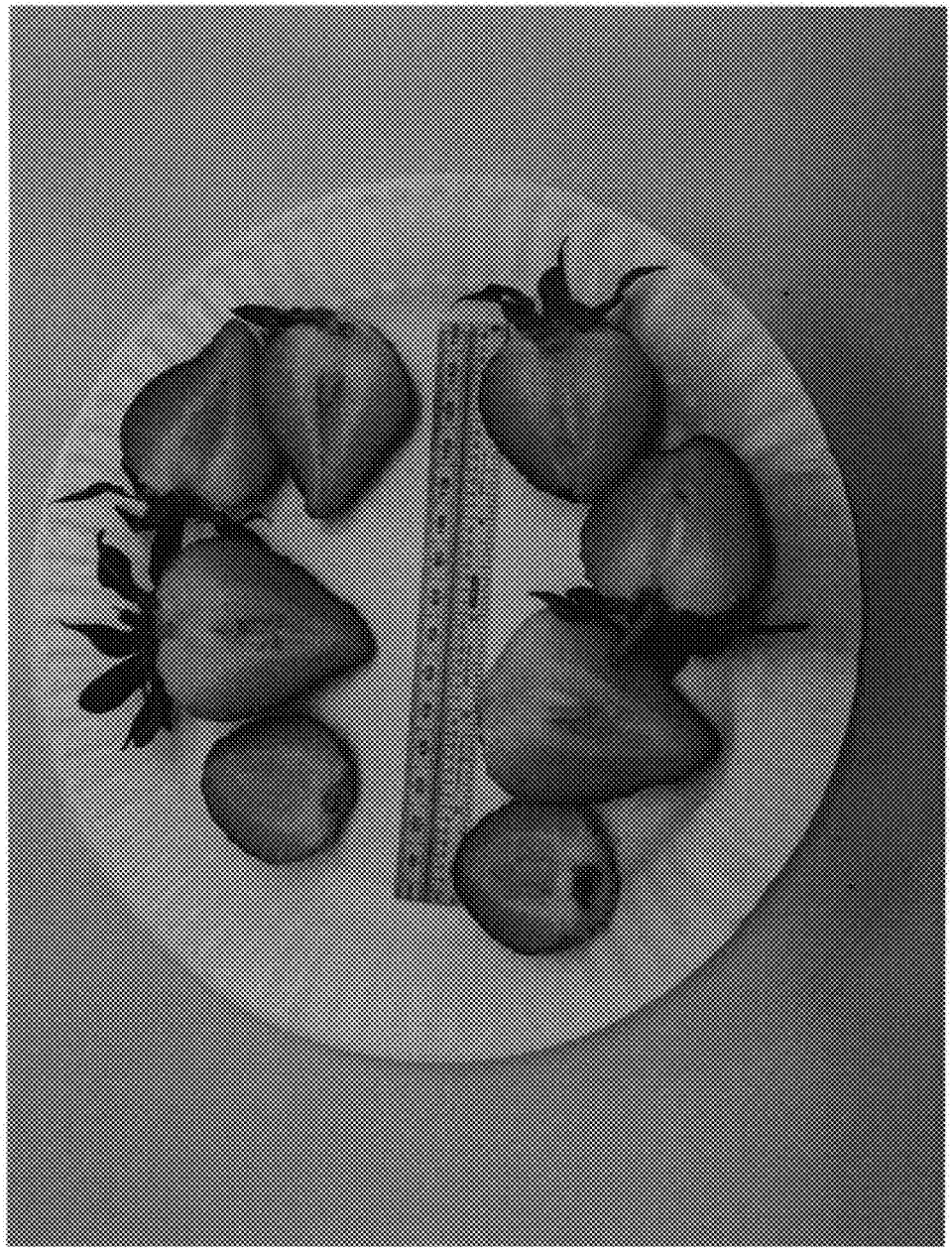
FIG. 8 shows fruits of 'Dr. Duncan' plants cut in half.

The invention claimed is:

1. A new and distinct cultivar of strawberry plant named 'Dr. Duncan', substantially as shown and described herein.

* * * * *